United States Patent [19]

Kume et al.

[11] Patent Number: 5,034,051
[45] Date of Patent: Jul. 23, 1991

[54] HETEROCYCLIC COMPOUNDS

[75] Inventors: Toyohiko Kume; Toshio Goto; Atsumi Kamochi; Katsuhiko Shibuya; Hiroshi Miyauchi, all of Tokyo, Japan

[73] Assignee: Nihon Tokushu Noyaku Seizo K.K., Tokyo, Japan

[21] Appl. No.: 370,424

[22] Filed: Jun. 23, 1989

[30] Foreign Application Priority Data

Jul. 4, 1988 [JP] Japan ................. 63-165040

[51] Int. Cl.$^5$ .............. A01N 43/72; A01N 43/58; C07D 265/36; C07D 487/02
[52] U.S. Cl. ........................... 71/92; 71/90; 71/88; 544/58.2; 544/105; 544/236
[58] Field of Search .............. 544/105, 58.2, 236; 71/90, 92

[56] References Cited

U.S. PATENT DOCUMENTS

| | | | |
|---|---|---|---|
| 4,619,687 | 10/1986 | Haga et al. | 544/105 |
| 4,640,707 | 2/1987 | Nagauo et al. | 544/105 |
| 4,786,310 | 11/1988 | Haga et al. | 546/121 |
| 4,804,394 | 2/1989 | Kume | 544/105 |
| 4,828,605 | 5/1989 | Haga et al. | 546/121 |

FOREIGN PATENT DOCUMENTS

| | | |
|---|---|---|
| 170191 | 2/1986 | European Pat. Off. |
| 0176101 | 4/1986 | European Pat. Off. |
| 0230874 | 8/1987 | European Pat. Off. |

Primary Examiner—C. Warren Ivy
Assistant Examiner—Celia Chang
Attorney, Agent, or Firm—Sprung Horn Kramer & Woods

[57] ABSTRACT

Herbicidal compounds of the formula

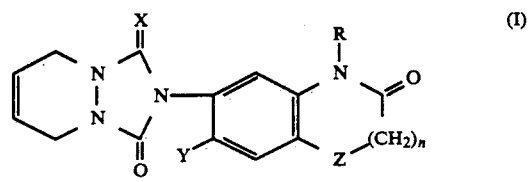

(I)

in which
X denotes an oxygen atom or sulfur atom,
Y denotes a hydrogen atom or halogen atom,
Z denotes an oxygen atom or sulfur atom,
n denotes 0 to 1, and
R denotes hydrogen, an alkyl group having 1 to 6 carbon atoms, an alkenyl group having 2 to 4 carbon atoms or an alkynyl group having 2 to 4 carbon atoms.

Intermediates of the formula

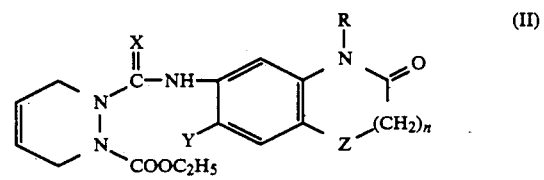

(II)

are also new.

8 Claims, No Drawings

HETEROCYCLIC COMPOUNDS

The present invention relates to novel heterocyclic compounds, to a process for their preparation, to their use as herbicides.

It has already been disclosed that certain benzoxazine compounds are useful as herbicides (see EP-OS Nos. 176,101 and 230,874).

There have been found novel heterocyclic compounds of the formula (I)

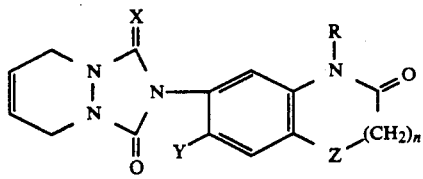

wherein X denotes an oxygen atom or sulfur atom,
Y denotes a hydrogen atom or halogen atom,
Z denotes an oxygen atom or sulfur atom,
n denotes 0 or 1, and
R denotes hydrogen, an alkyl group having 1 to 6 carbon atoms, preferably 1 to 4 carbon atoms, an alkenyl group having 2 to 4 carbon atoms or an alkynyl group having 2 to 4 carbon atoms.

The alkyl, alkenyl and alkynyl groups may be straight-chain or branched.

Heterocyclic compounds of the formula (I) are obtained by subjecting compounds of the formula (II)

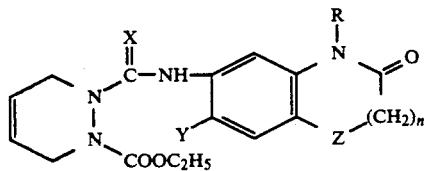

wherein, X, Y, Z, n and R have the foregoing definitions ring-closure, i.e. condensation, in the presence of condensing agents and inert solvents.

The novel heterocyclic compounds exhibit powerful herbicidal properties.

Surprisingly, the heterocyclic compounds according to the invention exhibit a substantially greater herbicidal action than those known from the prior art, for instance, aforementioned EP-OS Nos. 176,101 and 230,874, and a stable combating action against weeds in upland crop fields while exhibiting good compatibility with the crop.

Among the heterocyclic compounds according to the invention, of the formula (I), preferred compounds are those wherein X is an oxygen atom or sulfur atom,
Y is a hydrogen atom or fluorine atom,
Z is an oxygen atom or sulfur atom,
n is 0 or 1, and
R is hydrogen, an alkyl group having 1 to 3 carbon atoms, an alkenyl group having 2 to 3 carbon atoms or a propargyl group.

Very particularly preferred heterocyclic compounds of the formula (I) are those wherein X is an oxygen atom,
Y is a fluorine atom,
Z is an oxygen atom or sulfur atom,
n is 0 or 1, and
R is methyl, ethyl, n-propyl, iso-propyl, allyl or propargyl.

Specifically, the following compounds may be mentioned:

5,8-dihydro-2-(6-fluoro-3-propargyl-2-benzothiazolon-5-yl)-1H-[1,2,4]triazolo[1,2-a]pyridazine-1,3(2H)-dione, 5,8-dihydro-2-(6-fluoro-3-propargyl-2-benzothiazolon-5-yl)-1H-[1,2,4]triazolo[1,2-a]pyridazine-1-thion-3(2H)-one, 5,8-dihydro-2-(7-fluoro-4-propargyl-4H-1,4-benzoxazin-3(4H)-on-6-yl)-1H-[1,2,4]triazolo[1,2-a]pyridazine-1,3(2H)-dione, and 5,8-dihydro-2-(7-fluoro-4-propargyl-4H-1,4-benzoxazin-3(4H)-on-6-yl)-1H-[1,2,4]triazolo[1,2-a]pyridazine-1-thion-3(2H)-one.

If, for example, (2-ethoxycarbonyl-1,2,3,6-tetrahydropyridazin-1-yl-carbonylamino)-6-fluoro-3-propargyl-benzothiazol-2-one is employed, the reaction can be represented by the following equation:

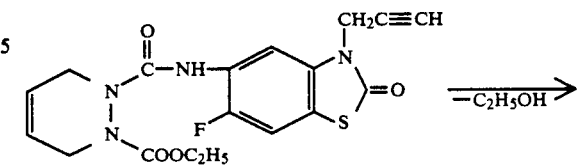

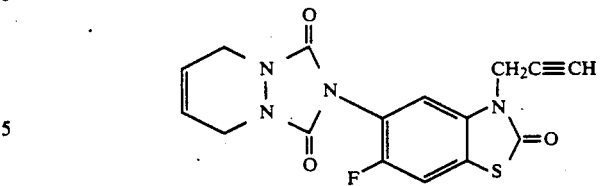

The compounds of the formula (II) are novel and can be obtained by reacting compounds of the formula (III)

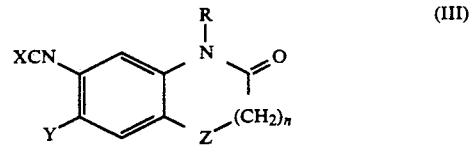

wherein X, Y, Z, n and R have the foregoing definitions,
with 2-ethoxycarbonyl-1,2,3,6-tetrahydropyridazine, in the presene of inert solvents, such as toluene.

The compounds of the formula (III) are already known (see Japanese Patent Laid-open 152683/1986). As examples there may be mentioned:

6-fluoro-5-isocyanato-3-propargylbenzothiazol-2-one,
6-fluoro-5-isothiacyanato-3-propargylbenzothiazol-2-one, and
7-fluoro-6-isocyanato-4-propargyl-4H-1,4-benzoxazin-3-one.

As appropriate diluents for carrying out the process, any kind of inert organic solvents can be mentioned.

As the examples of such diluents, use may be made of water, aliphatic, cycloaliphatic and aromatic hydrocarbons, which may or may not be chlorinated, such as, for example, hexane, cyclohexane, petroleum ether, ligroin, benzene, toluene, xylene, methylene chloride, chloroform, carbon tetrachloride, ethylene chloride, chlorobenzene, and further; ethers such as, for example, diethyl ether, methylethyl ether, di-iso-propyl ether, dibutyl ether, propylene oxide, dioxane, tetrahydrofuran; ketones such as, for example, acetone, methylethyl ketone, methyl-iso-propyl ketone, methyl-iso-butyl ketone; nitriles such as, for example, acetonitrile, propionitrile, acrylonitrile; alcohols such as methanol, ethanol, iso-propanol, butanol, ethylene glycol; esters such as, for example, ethyl acetate, amyl acetate; acid amides such as, for example, dimethylformamide, dimethylacetamide; sulfones and sulfoxides such as, for example, dimethylsulfoxide, sulfolane; and bases such as, for example, pyridine, etc.

In carrying out the process, use of a catalyst is preferable and, as the catalyst, may be mentioned, for example, sodium methoxide, sodium ethoxide, sodium hydroxide and potassium hydroxide.

The reaction temperature of the process may vary in a fairly wide range. In general, the reaction is carried out at a temperature of about 30° to 150° C., preferably a temperature of about 40° to 90° C. It is preferred to carry out the reaction under normal pressure, although a higher or lower pressure can also be used.

In the process, the desired compound can be obtained by subjecting the compound having the general formula (II), for example, to a ring-closing condensation reaction in an inert solvent such as methanol and in the presence of a catalytic amount of sodium methoxide.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Isochaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters; ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.0001 and 2 kg of active compound per hectare of soil surface, preferably between 0.001 and 1 kg per ha.

The preparation and use of the active compounds according to the invention can be seen from the following examples.

PREPARATIVE EXAMPLES

EXAMPLE 1

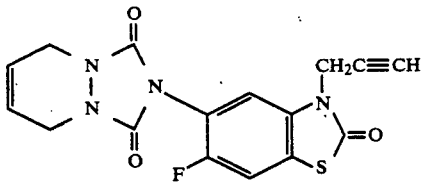

2 gr. of 6-fluoro-5-isocyanato-3-propargyl-2-benzothiazolone were dissolved in 20 ml of toluene and, to the solution, were added dropwise 1.32 gr. of 2-ethoxycarbonyl-1,2,3,6-tetrahydropyridazine at room temperature, followed by a six hour-stirring at room temperature and distilling-off of the solvent therefrom at reduced pressure.

To the residue were added 60 ml of methanol and 10 mg. of sodium methoxide followed by a four-hour heating under reflux. The reaction mixture was stirred for 30 minutes at a temperature in the range of from 10° to 20° C. and the resulting solid was filtered therefrom, washed with methanol and toluene and dried to obtain 1.2 g of the desired 5,8-dihydro-2-(6-fluoro-3-propargyl-2-benzothiazolone)-1H-[1,2,4]triazolo-[1,2-a]pyridazine-1,3(2H)-dione having a melting point of 274° to 278° C.

In place of 6-fluoro-5-isocyanato-3-propargyl-2-benzothiazolone in the foregoing Example 1, use was made of 6-fluoro-5-isothiocyanato-3-propargyl-2-benzothiazolone and 7-fluoro-6-isocyanato-4-propargyl-4H-1,4-benzoxazin-3-one so as to obtain 5,8-dihydro-2-(6-fluoro-3-propargyl-2-benzothiazolon-5-yl)-1H-[1,2,4]triazolo-[1,2-a]pyridazine-1-thion-3(2H)-one and 5,8-dihydro-2-(7-fluoro-4-propargyl-4H-1,4-benzoxazin-3(4H)-on-6-yl)-1H-[1,2,4]triazolo-[1,2-a]pyridazine-1,3(2H)-dione, respectively.

In the following Table 1 are shown the compounds of the present invention which can be prepared by the same process as that employed in Example 1 together with compounds which were actually prepared by the examples according to the present invention.

TABLE 1

| Compound No. | X | Y | Z | n | R | mp. (°C.) |
|---|---|---|---|---|---|---|
| 1 | O | F | S | 0 | CH$_3$ | |
| 2 | O | F | S | 0 | C$_2$H$_5$ | |
| 3 | O | F | S | 0 | C$_3$H$_7$-n | |
| 4 | O | F | S | 0 | CH$_2$CH=CH$_2$ | |
| 5 | O | F | S | 0 | CH$_2$C≡CH | 274–278 |
| 6 | S | F | S | 0 | CH$_2$C≡CH | 253–257 |
| 7 | O | F | O | 1 | H | >300 |
| 8 | O | F | O | 1 | H | 293–298 |
| 9 | O | F | O | 1 | CH$_3$ | |
| 10 | O | F | O | 1 | C$_2$H$_5$ | |
| 11 | O | F | O | 1 | C$_3$H$_7$-n | |
| 12 | O | F | O | 1 | CH$_2$CH=CH$_2$ | |
| 13 | O | F | O | 1 | CH$_2$C≡CH | 258–262 |
| 14 | S | F | O | 1 | CH$_2$C≡CH | 231–235 |
| 15 | O | H | O | 1 | CH$_2$CH=CH$_2$ | |
| 16 | S | H | O | 1 | CH$_2$CH=CH$_2$ | |
| 17 | O | H | O | 1 | CH$_2$C≡CH | |
| 18 | S | H | O | 1 | CH$_2$C≡CH | |

COMPARATIVE EXAMPLE (PREPARATION OF MATERIAL COMPOUND)

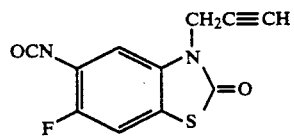

To a solution consisting of 3.2 g of 5-amino-6-fluoro-3-propargyl-2-benzothiazolone and 50 g of dioxane were dropwise added 2.4 g of trichloromethyl chlorocarbonate at a temperature in the range of from 5° to 15° C. and the resulting mixture was heated under reflux for six hours. A residue was obtained by distilling off the low-boiling material from the mixture under reduced pressure, and it was dissolved in 150 ml of dried toluene and filtered. From the resulting filtrate toluene was distilled off to obtain 3.6 g of 6-fluoro-5-isocyanato-3-propargyl-2-benzothiazolone having a melting point in the range from 134° to 135° C.

BIOTEST EXAMPLE

Known compounds employed for comparison

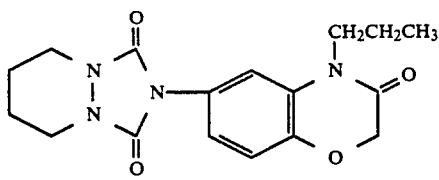

(disclosed by European Patent Application Disclosure No. 176,101/Compound No. 2)

EXAMPLE 2

Test on weeds in a flooded paddy by water surface application

Preparation of an active compound formulation

Carrier: 5 parts by weight of acetone

Emulsifier: 1 part by weight of benzyloxy polyglycol ether

A formulation of an active compound was obtained as an emulsifiable concentrate by mixing 1 part by weight of the active compound with the above-mentioned amounts of the carrier and the emulsifying agent. A predetermined amount of the formulation was diluted with water.

Testing method

Paddy soil was filled in pots (1/2,000 are; 25×20×9 cm), and rice seedlings (variety: "Nihonbare") in the 2.5-leaf stage (15 cm tall) were transplanted at two places per pot each as a stock of three seedlings. Seeds of barnyard grass (Echinochloa oryzicola Vasing.), umbrella plant (Cyperus difformis L.), monochoria (Monochoria vaginalis), and annual broadleaved weeds false pimpernel (Lindernia pyxidaria L.), Rotala indica, American waterwort (Elatine triandra), red stem (Ammannia multiflora Roxburgh) and Dopatrium junceum Hamilton were sown and the pots were maintained wet. Two days later, the pots were flooded to a depth of about 2 to 3 cm. Five days after the transplantation of the seedlings, the compound of this invention, in the form of an emulsifiable concentrate as prepared above, was applied to the water surface by a pippette in a predetermined amount. Thereafter, the flooded condition of about 3 cm was maintained, and four weeks after the chemical treatment, the herbicidal effect and the phytotoxicity to rice were evaluated and rated on the scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect)

Phytotoxicity to crop (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity)

The test results are shown in Table 2 by typical examples.

TABLE 2

| Active compound No. | Amount of active compound (kg/ha) | Herbicidal effect on weeds | | | | Phytotoxic effect on rice plants |
|---|---|---|---|---|---|---|
| | | Barnyard grass | Umbrella plant | Monochoria | Annual broad-leaved grass | |
| 5 | 0.125 | 4 | 5 | 5 | 5 | 1 |
|   | 0.06 | 3 | 5 | 5 | 5 | 0 |
| 13 | 0.125 | 5 | 5 | 5 | 5 | 2 |
|   | 0.06 | 4 | 5 | 5 | 5 | 0 |
| (Control compound) | | | | | | |
| E-1 | 0.25 | 2 | 3 | 3 | 3 | 3 |
|   | 0.125 | 1 | 3 | 2 | 2 | 2 |

EXAMPLE 3

Test on upland weeds by soil treatment before emergence

In a greenhouse, soybean seeds were sown in 500 cm² pots filled with upland farm soil, and soil containing seeds of barnyard grass (Echinochloa crus-galli), wild blite (Amaranthus blitum L.) and goosefoot (Chenopodium album L.) was put over the soil in the pots in a depth of 1 cm.

One day after the sowing, a test chemical in a predetermined concentration, prepared as in Example 2, was uniformly sprayed over the surface layer of the soil in each of the test pots.

Four weeks after the spraying, the herbicidal effect and the phytotoxicity to crops were examined on the same standards as in Example 2. The results are shown in Table 3.

TABLE 3

| Active compound No. | Amount of active compound (kg/ha) | Herbicidal effect on weeds | | | Phytoxic effect on soy bean plants |
|---|---|---|---|---|---|
| | | Barnyard grass | Wild blite | Goose-foot | |
| 5 | 0.125 | 5 | 5 | 5 | 1 |
|   | 0.06 | 4 | 5 | 5 | 0 |
| 13 | 0.125 | 5 | 5 | 5 | 1 |
|   | 0.06 | 4 | 5 | 5 | 0 |
| (Control compound) | | | | | |
| E-1 | 0.25 | 1 | 3 | 3 | 2 |
|   | 0.125 | 0 | 1 | 2 | 1 |

EXAMPLE 4

Test on upland farm weeds by foliar treatment

In a greenhouse, corn seeds were sown in 500 cm² pots filled with upland farm soil, and soil containing seeds of Fingergrass (*Digitaria sanguinalis*), wild blite (*Amaranthus blitum* L.) and goosefoot (*Chenopodium album* L.) was put over the soil in the pots in a depth of 1 cm.

After sowing, the plants were grown for 14 days and a test chemical in a predetermined concentration, prepared as in Example 2, was uniformly sprayed over the test plants in each of the test pots.

Four weeks after the spraying, the herbicidal effect and the phytotoxicity to crops were examined on the same standards as in Example 2. The results are shown in Table 4.

TABLE 4

| | Amount of active compound (kg/ha) | Herbicidal effect on weeds | | | Phytotoxicity on corn plants |
|---|---|---|---|---|---|
| | | Finger-grass | Wild blite | Goose-foot | |
| Active compound No. | | | | | |
| 5 | 0.06 | 5 | 5 | 5 | 1 |
| | 0.03 | 5 | 5 | 5 | 0 |
| 13 | 0.06 | 5 | 5 | 5 | 1 |
| | 0.03 | 5 | 5 | 5 | 0 |
| (Control compound) | | | | | |
| E-1 | 0.125 | 2 | 3 | 3 | 3 |
| | 0.06 | 1 | 2 | 2 | 2 |

It will be appreciated that the instant specification and claims are set forth by way of illustration and not limitation, and that various modifications and changes may be made without departing from the spirit and scope of the present invention.

What is claimed is:

1. A heterocyclic compound of the formula

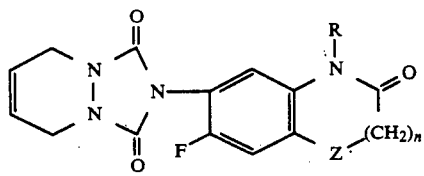

in which
Z denotes an oxygen atom or sulfur atom,
n denotes 0 or 1, and
R denotes an alkynyl group having 2 to 4 carbon atoms.

2. A compound according to claim 1, in which R denotes a propargyl group.

3. A compound according to claim 1, wherein such compound is 5,8-dihydro-2-(6-fluoro-3-propargyl-2-benzothiazolon-5-yl)-1H-[1,2,4]triazolo[1,2-a]pyridazine-1,3(2H)-dione of the formula

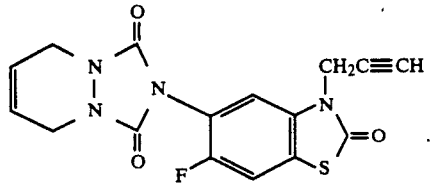

4. A compound according to claim 1, wherein such compound is 5,8-dihydro-2-(7-fluoro-4-propargyl-4H-1,4-benzoxazin-3(4H)-on-6-yl)-1H-[1,2,4]triazolo[1,2-a]pyridazine-1,3(2H)-dione of the formula

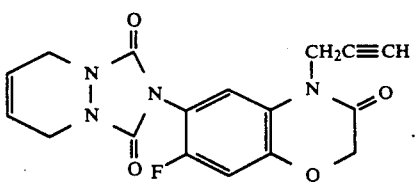

5. A herbicidal composition comprising a herbicidally effective amount of a compound according to claim 1, and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is
5,8-dihydro-2-(6-fluoro-3-propargyl-2-benzothiazolon-5-yl)-1H-[1,2,4]triazolo[1,2-a]pyridazine-1,3(2H)-dione, or
5,8-dihydro-2-(7-fluoro-4-propargyl-4H-1,4-benzoxazin-3(4H)-on-6-yl)-1H-[1,2,4]triazolo[1,2-a]pyridazine-1,3(2H)-dione.

8. A compound of the formula

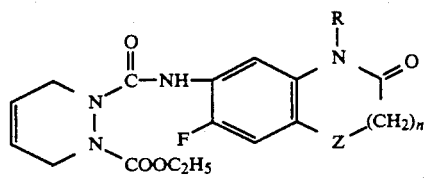

in which
Z denotes an oxygen atom or sulfur atom,
n denotes 0 or 1, and
R denotes an alkynyl group having 2 to 4 carbon atoms.

* * * * *